(12) United States Patent
Lindstedt Alstermark et al.

(10) Patent No.: US 7,462,644 B2
(45) Date of Patent: *Dec. 9, 2008

(54) THERAPEUTIC AGENTS

(75) Inventors: Eva-Lotte Lindstedt Alstermark, Mölndal (SE); Anna Christina Olsson, Mölndal (SE); Lanna Li, Mölndal (SE); Carl-Johan Aurell, Södertälje (SE); Anna Minidis, Södertälje (SE); Esmail Yousefi-Salakdeh, Södertälje (SE); Mikael Ulf Johan Dahlström, Mölndal (SE)

(73) Assignee: AstraZeneca AB (SE)

( * ) Notice: Subject to any disclaimer, the term of this patent is extended or adjusted under 35 U.S.C. 154(b) by 194 days.

This patent is subject to a terminal disclaimer.

(21) Appl. No.: 10/499,893

(22) PCT Filed: Dec. 19, 2003

(86) PCT No.: PCT/GB03/05602

§ 371 (c)(1),
(2), (4) Date: Jun. 23, 2004

(87) PCT Pub. No.: WO2004/056748

PCT Pub. Date: Jul. 8, 2004

(65) Prior Publication Data

US 2005/0131068 A1    Jun. 16, 2005

(30) Foreign Application Priority Data

Dec. 21, 2002    (GB)    .................. 0229931.1

(51) Int. Cl.
*A61K 31/19*    (2006.01)
*C07C 229/00*    (2006.01)

(52) U.S. Cl. ...................... 514/568; 562/450
(58) Field of Classification Search ........ 514/568; 562/450
See application file for complete search history.

(56) References Cited

U.S. PATENT DOCUMENTS

| | | | |
|---|---|---|---|
| 2,928,840 | A | 3/1960 | Shapiro et al. |
| 3,244,398 | A | 4/1966 | Scaramamucci |
| 4,735,959 | A | 4/1988 | Grell |
| 5,210,208 | A | 5/1993 | Huang et al. |
| 5,216,167 | A | 6/1993 | Grell et al. |
| 6,143,769 | A | 11/2000 | Grell et al. |
| 6,258,850 | B1 | 7/2001 | Andersson |
| 6,410,585 | B1 | 6/2002 | Larsen et al. |
| 6,596,751 | B2 | 7/2003 | Fujita et al. |
| 6,884,821 | B1 | 4/2005 | Shinoda et al. |
| 7,256,307 | B2 | 8/2007 | Lindstedt et al. |
| 2005/0148656 | A1 | 7/2005 | Li et al. |
| 2005/0171204 | A1 | 8/2005 | Lindstedt et al. |
| 2005/0282822 | A1 | 12/2005 | Alstermark et al. |
| 2006/0111406 | A1 | 5/2006 | Crespo et al. |
| 2006/0142389 | A1 | 6/2006 | Aurell et al. |
| 2006/0142392 | A1 | 6/2006 | Aurell et al. |
| 2006/0194879 | A1 | 8/2006 | Ragnar et al. |
| 2006/0258866 | A1 | 11/2006 | Li et al. |

FOREIGN PATENT DOCUMENTS

| | | |
|---|---|---|
| BE | 660266 | 8/1965 |
| DE | 266121 | 10/1913 |
| DE | 807687 | 7/1951 |
| DE | 1935758 | 2/1970 |
| DE | 2130282 | 12/1971 |
| DE | 2160380 | 6/1973 |
| DE | 2828222 | 1/1980 |
| EP | 1167357 | 10/2000 |
| FR | 2245624 | 4/1975 |
| JP | 2001-261612 | 9/2001 |
| WO | WO 92/05145 | 4/1992 |
| WO | WO 96/40201 | 12/1996 |
| WO | WO 99/11606 | 3/1999 |
| WO | WO 99/24442 | 5/1999 |
| WO | WO 00/59889 | 10/2000 |
| WO | WO 00/61582 | 10/2000 |
| WO | WO 00/61585 | 10/2000 |
| WO | WO 00/63196 | 10/2000 |
| WO | WO 00/64888 | 11/2000 |
| WO | WO 00/75103 | 12/2000 |
| WO | WO 01/25181 | 12/2001 |
| WO | WO 02/44127 | 6/2002 |

(Continued)

OTHER PUBLICATIONS

Adamczyk, Maciej, et al., "Use of Lipase for Regioselective One Pot Amidation and Hydrolysis," HCAPLUS 130:251916 (1999).

(Continued)

*Primary Examiner*—Taylor Victor Oh
(74) *Attorney, Agent, or Firm*—Fish & Richardson P.C.

(57) ABSTRACT

The present invention provides the S enantiomer of a compound of formula I

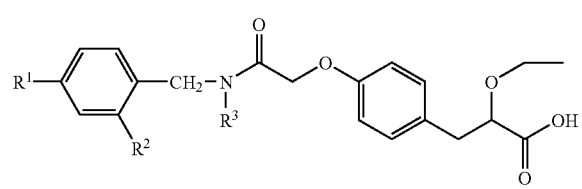

wherein $R^1$ represents chloro, trifluoromethyl or trifluoromethoxy, $R^2$ represents H or fluoro and $R^3$ represents a $C_{2-4}$alkyl group as well as pharmaceutically acceptable salts, solvates and prodrugs thereof, to processes for preparing such compounds, to their the utility in treating clinical conditions including lipid disorders (dyslipidemias) whether or not associated with insulin resistance, to methods for their therapeutic use and to pharmaceutical compositions containing them.

18 Claims, No Drawings

FOREIGN PATENT DOCUMENTS

| WO | WO 02/44130 | 6/2002 |
|---|---|---|
| WO | WO 02/064549 | 8/2002 |
| WO | WO 02/083616 | 10/2002 |
| WO | WO 03/051822 A1 | 3/2003 |
| WO | WO 03/051821 A1 | 6/2003 |
| WO | WO 2004/056748 A1 | 7/2004 |
| WO | WO 2004/000789 A1 | 12/2004 |
| WO | WO 2004/113270 A1 | 12/2004 |

OTHER PUBLICATIONS

Azzolina, Ornella, et al. "Antiphlogistics Aryloxypropionic Acids: Configurational Study," HCAPLUS 120:133356 (1994).
Bagley, Scott, et al., "Phenoxyphenylacetic Acids and Derivatives Useful as Endothelin Antagonists," HCAPLUS 125:328289 (1996).
Bagley, Scott, et al., "Preparation of Phenoxyphenlacetic Acid-Derivative Endothelin Antagonists," HCAPLUS 125:58490 (1996).
Bagley, Scott, et al., "Preparation of Phenoxyphenylacetates and Analogs as Endothelin Receptor Antagonist," HCAPLUS 129:67607 (1998).
Barrie, S. E. et al., "A Reappraisal of the Effect Upon Thymidine Kinase of Thymidine Derivatives Carrying Large Groups at the 5'-Position," J. Med. Chem., vol. 27, No. 8, pp. 1044-1047 (1984).
Bauer, Klaus, et al., "Phenoxyalkane- and pheroxyalkene Carboxylic Acid, Their Derivatives and Their Use," HCAPLUS 96:7068 (1982).
Beckh, Hansjoerg, et al., "Preparation of Sulfonamides Containing Tetrazolyl Groups and Their Use as Drugs," HCAPLUS 113:59148 (1990).
Berge, John, et al., "Tertiary Phenethylamines," HCAPLUS 104:5623 (1986).
Bohlmann, Ferdinand, et al., "Polyacetylene Compounds CIX. Synthesis of Natrally Occurring, Aromatic substituted Acetylene compounds," HCAPLUS 65:99100 (1966).
Chandrakumar, Nizal Samuel, et al., "LTA4-Hydrolase Inhibitors, Pharmaceutical Compositions, and Methods of Use," HCAPLUS 125:142725 (1996).
Chandrakumar, Nizal Samuel, et al., "Preparation of Heterocyclic LTA4 Hydrolase Inhibitors," HCAPLUS 125:142545 (1996).
De Marchi, F., et al., "Synthesis and Pharmacological Evaluation of Some N-diethylaminoethylaryloxyacetamides and related Compounds," HCAPLUS 79:78343 (1973).
Eakin Murdoch Allan, et al., "Preparation on N-(2-phenoxyethyl)-2-hydroxy-3-thienyloxypropylamines and Analogs as Thermogentic Agents," HCAPLUS 114:163992 (1991).
Fex, Thomas, et al., "Preparation of N-aralkoxy-N-aralkylureas and Analogs as Antitumor Agents," HCAPLUS 124:201795 (1995).
Cantello, Barrie Christian Charles, "2-Aminoethyl Ether Derivatives, and Their Pharmaceutical Composition," HCAPLUS 101:6799 (1984).
Greenlee, William J., et al., "Phenoxyphenylacetic Acid Derivatives Useful as Endothelin Antagonists," HCAPLUS 122:31129 (1995).
Hankovszky, H. O., et al., "Benzazoles. VI. O-Alkylation of 2-(hydroxyphenyl)- and 2-(hydroxybenzyl) Benzazoles," HCAPLUS 69:106619 (1968).
Harvey, Charolette, M., et al., "Preparation of Endothelin Receptor Antagonists for the Treatment of Ernesis," HCAPLUS 125:114587 (1996).
Hayashi, Tetsuyoshi, et al., "Insect Juvenile Hormone Mimetic activity of (4-substituted)phenoxyalkyl Compounds with Various Nitrogenous and Oxygenous Functions and Its Relationship to Their Electrostatic and Stereochemical Properties," HCAPLUS 115:250297 (1991).
Hideg, Kalman, et al., "Alkylbenzazoles," HCAPLUS 69:36127 (1968).
Iijima, Ikuo, et al., "Preparation of [(sulfonylamino)phenoxy]alkanoic acids as Antilipemics," HCAPLUS 118:6741 (1993).
Iijima, Ikuo, et al., "Preparation of p-(sulfonylaminoalkyl)phenoxyalkanoic Acid Derivatives as Antilipidemics," HCAPLUS 121:82733 (1994).
Iwakuma, Takeo, et al., "Phenoxyacetic ACids as Thromboxane A2 Antagonists and Their Preparation," HCAPLUS 112:76612 (1990).
Iwamura, Hajime, et al., "Preparation of Phenolic Ethers as Insecticides," HCAPLUS 116:128359 (1992).
Kraska, Allen R., "Compounds Derived from Formylphenoxyacetic Acid as Antiviral Agents in Animals," HCAPLUS 96:34915 (1982).
Large, M. S., Smith, L.H., "β-Asrenergic Blocking Agents. 23. 1-[(Substituted-amindo)phenoxy]-3-[[(substituted-amido)alkyl]amino]propan-2-ols," J. Med. Chem., vol. 26, No. 3, pp. 352-357 (1983).
Nametkin, et al., "Synthesis of Some Alkyl- and Aralkylphenoxyactic Acids and Their Derivatives," ZH. Obshch. Khim., 21, pp. 2146-2147 (1951).
Nametkin, S. S., et al., "Synthesis of Some Alkyl- and Aralkylphenoxyacetic Acids and Their Derivatives," HCAPLUS 46:48488 (1952).
Penning, Thomas D. et al., "Structure-Activity Relationship Studies on 1-[2-(4-Phenylphenoxy)ethyl]pyrrolidine (SC-22716), a Potent Inhibitor of Leukotriene $A_4$ ($LTA_4$) Hydrolase," HCAPLUS 132:245841 (2000).
Reiffen, Manfred, et al., "Preparation of 2-thiazolyl- and 2-oxazolyl-2-alkoxy-1-aminoethane Derivatives as Antidiabetics and Antiobesity Agents," HCAPLUS 108:221694 (1988).
Reiffen, Manfred, et al., "Preparation of Oxazole- and Thiazoleethanamines as Antidiabetics, Antiatherosclerotics, and Antiobesity Agents," HCAPLUS 108:150463 (1988).
Sano, Hidekazu, et al., "Reversible Thermal Printing Material Containing Imide Compounds as Decoloration Accelerator," HCAPLUS 136:191709 (2002).
Sano, Hidekazu, et al., "Reversible Thermal Recording Material Containing Cyano Compound as Decoloration Accelerator," HCAPLUS 136:175486 (2002).
Sasaki, Yasuhiko, et al., "Preparation of 4-(2-sulfonylaminoethyl)phenol Ethers as Thromboxane A2 Antagonists," HCAPLUS 116:105828 (1992).
Stubenrauch, Gerd, et al., "Fungicidal 1,2,4-triazol-1-yl Compounds," 94:15736 (1981).
Svab, A., et al., "Some 3-substituted Derivatives of 5-methylisoxazole with an Antiparasitic Effect," HCAPLUS 100:82623 (1984).
Tamiz, Amir P., et al., "Structure-Activity Relationship of N-(Phenylalkyl) Cinnamides as Novel NR2B Subtype-Selective NMDA Receptor Antagonists," HCAPLUS 131:252095 (1999).
Willson T. M. et al.: "The PPARs: From Orphan Receptor to Drug Discovery," Journal of Medicinal Chemistry, American Chemical Society, vol. 43, No. 4, pp. 527-550 (2000).
Witte Ernst Christian, et al., "Phenoxyalkylcarboxylic Acid Derivatives," HCAPLUS 92:6247 (1980).
Witte, Ernst Christian, et al., "Preparation of (sulfonylaminoalkyl)phenoxyacyl Amino Acids as Cardiovascular Agents," HCAPLUS 115:280555 (1991).
Witte, Ernst, et al., "N-[[(aminoalkyl)phenyl]alkyl]- and N-[[(aminoalkoxy)phenyl]alkyl]sulfonamides, a Process for Their Preparation and Their Use as Thromboxane Antagonists," HCAPLUS 117:170993 (1992).
Kirk-Othmer Encyclopedia of Chemical Technology, Copyright © 2002 by John Wiley & Sons, Inc., pp. 95-147, Article Online Posting Date: Aug. 16, 2002.
Randle, Philip J. et al., "Glucose Fatty Acid Interactions and the Regulation of Glucose Disposal", Journal of Cellular Biology 55S:1-11 (1994).
Rouhi, A. Muareen et al., "The Right Stuff. From research and development to the clinic, getting drug crystals right is full of pitfalls", Chemical & Engineering News, pp. 32-35 (2003).
Silverman, Richard B., "The Organic Chemistry of Drug Design and Drug Action", pp. 19-23 (1992).
Wikipedia website on "Prodrug" htpp://em.wikipedia.org/wiki/Prodrug dated Dec. 5, 2006.

THERAPEUTIC AGENTS

CROSS-REFERENCE TO RELATED APPLICATIONS

This application is the national phase application under 35 U.S.C. §371 of PCT International Application No. PCT/GB03/05602, filed Dec. 19, 2003, which claims priority to United Kingdom Application Ser. No. 0229931.1, filed Dec. 21, 2002.

FIELD OF THE INVENTION

The present invention relates to certain novel (2S)-3-(4-{2-[amino]-2-oxoethoxy}phenyl)-2-ethoxypropanoic acid derivatives, to processes for preparing such compounds, to their utility in treating clinical conditions including lipid disorders (dyslipidemias) whether or not associated with insulin resistance and other manifestations of the metabolic syndrome, to methods for their therapeutic use and to pharmaceutical compositions containing them.

BACKGROUND OF THE INVENTION

The metabolic syndrome including type 2 diabetes mellitus, refers to a cluster of manifestations including insulin resistance with accompanying hyperinsulinaemia, possibly type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in patients with the metabolic syndrome and thus to correct the dyslipidaemia which is considered to cause the accelerated progress of atherosclerosis. However, currently this is not a universally accepted diagnosis with well-defined pharmacotherapeutic indications.

The S-enantiomer of the compound of formula C below

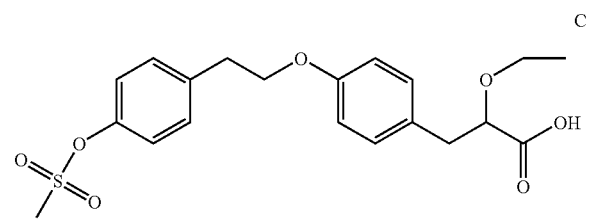

C 2-ethoxy-3-[4-(2-{4-methanesulfonyloxyphenyl}ethoxy)phenyl]propanoic acid, is disclosed in PCT Publication Number WO99/62872. This compound is reported to be a modulator of peroxisome proliferator-activated receptors (PPAR, for a review of the PPARs see T. M. Willson et al, J Med Chem 2000, Vol 43, 527) and has combined PPARα/PPARγ agonist activity (Structure, 2001, Vol 9, 699, P. Cronet et al). This compound is effective in treating conditions associated with insulin resistance.

Surprisingly a series of compounds has now been found which are selective PPARα modulators.

DESCRIPTION OF THE INVENTION

The present invention provides the S enantiomer of a compound of formula I

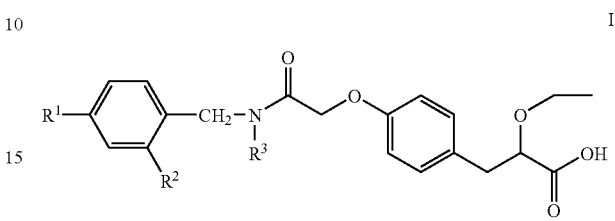

I wherein $R^1$ represents chloro, trifluoromethyl or trifluoromethoxy, $R^2$ represents H or fluoro and $R^3$ represents a $C_{2-4}$alkyl group as well as pharmaceutically acceptable salts, solvates and prodrugs thereof.

The term "prodrug" as used in this specifictation includes derivatives of the carboxylic acid group which are converted in a mammal, particularly a human, into the carboxylic acid group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy are known in the art. For examples of such prodrug derivatives, see:

a) Design of Prodrugs, edited by H. Bundgaard, (Elsevier, 1985) and Methods in Enzymology. 42: 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8:1-38 (1992);

d) H. Bundgaard, et al., Journal of Pharmaceutical Sciences, 77:285 (1988); and e) N. Kakeya, et al., Chem Pharm Bull, 32:692 (1984).

The above documents a to e are herein incorporated by reference.

In vivo cleavable esters are just one type of prodrug of the parent molecule. An in vivo hydrolysable (or cleavable) ester of a compound of the formula (I) that contains a carboxy group is, for example, a pharmaceutically acceptable ester which is hydrolysed in the human or animal body to produce the parent acid. Suitable pharmaceutically acceptable esters for carboxy include $C_{1-6}$alkoxymethyl esters, for example, methoxymethyl; $C_{1-6}$alkanoyloxymethyl esters, for example, pivaloyloxymethyl; phthalidyl esters; $C_{3-8}$cycloalkoxycarbonyloxy$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl; and may be formed at any carboxy group in the compounds of this invention.

Specific compounds of the invention are:
(2S)-3-[4-(2-{Butyl[2-fluoro-4-(trifluoromethyl)benzyl] amino}-2-oxoethoxy)phenyl]-2ethoxy propanoic acid;

(2S)-3-(4-{2-[(4-Chlorobenzyl)(ethyl)amino]-2-oxoethoxy}phenyl)-2-ethoxypropanoic acid;
(2S)-2-Ethoxy-3-[4-(2-{ethyl[4-(trifluoromethoxy)benzyl]amino)}-2-oxoethoxy)phenyl]-propanoic acid;
(2S)-2-Ethoxy-3-[4-(2-{ethyl[4-(trifluoromethyl)benzyl]amino}-2-oxoethoxy)phenyl]-propanoic acid; and
(2S)-3-[4-(2-{Butyl[4-(trifluoromethyl)benzyl]amino}-2-oxoethoxy)phenyl]-2-ethoxypropanoic acid;

and pharmaceutically acceptable salts and solvates thereof.

It should be understood that each of the above compounds individually and also any combination of these compounds for example two, three, four or all of the above compounds forms part of the present invention.

It should also be understood that the present invention includes the five embodiments in which each of the above five compounds is in turn excluded from the generic claim to a compound of formula I, as described above, by means of a proviso to that compound. The present invention also includes embodiments wherein any combination of the five compounds above is excluded from the generic claim to a compound of formula I, as described above, by means of a proviso to that combination of compounds.

In the present specification the expression "pharmaceutically acceptable salts" is intended to define but is not limited to base salts such as the alkali metal salts, alkaline earth metal salts, ammonium salts, salts with basic amino acids, and salts with organic amines, particularly tert-butylamine.

In another aspect the present invention provides one or more of the following:
(2S)-3-[4-(2-{Butyl[2-fluoro-4-(trifluoromethyl)benzyl]amino}-2-oxoethoxy)phenyl]-2-ethoxy propanoic acid tert-butylammonium salt;
(2S)-3-(4-{2-[(4-Chlorobenzyl)(ethyl)amino]-2-oxoethoxy}phenyl)-2-ethoxypropanoic acid tert-butylammonium salt;
(2S)-2-Ethoxy-3-[4-(2-{ethyl[4-(trifluoromethoxy)benzyl]amino}-2-oxoethoxy)phenyl]-propanoic, acid tert-butylammonium salt;
(2S)-2-Ethoxy-3-[4-(2-{ethyl[4-(trifluoromethyl)benzyl]amino}-2-oxoethoxy)phenyl]propanoic acid tert-butylammonium salt; and
(2S)-3-[4-(2-{Butyl[4-(trifluoromethyl)benzyl]amino}-2-oxoethoxy)phenyl]-2-ethoxypropanoic acid tert-butylammonium salt.

These salts may be prepared by reacting an acid with tert-butylamine (for example around a molar equivalent with respect to the acid) in a solvent for example an ether e.g. diisopropyl ether or tert-butylmethyl ether or an ester e.g. tert-butyl acetate or mixtures thereof or from a mixture of one of these solvents and an anti-solvent for example a hydrocarbon e.g. isooctane and isolating the salt by methods known to those skilled in the art for example by filtration.

It will also be understood that certain compounds of the present invention may exist in solvated, for example hydrated, as well as unsolvated forms. It is to be understood that the present invention encompasses all such solvated forms. Certain compounds of the present invention may exist as tautomers. It is to be understood that the present invention encompasses all such tautomers.

Methods of Preparation

The compounds of the invention may be prepared as outlined below. However, the invention is not limited to these methods. The compounds may also be prepared as described for structurally related compounds in the prior art. The reactions can be carried out according to standard procedures or as described in the experimental section.

Compounds of formula I may be prepared, by reacting the S-enantiomer of a compound of formula II

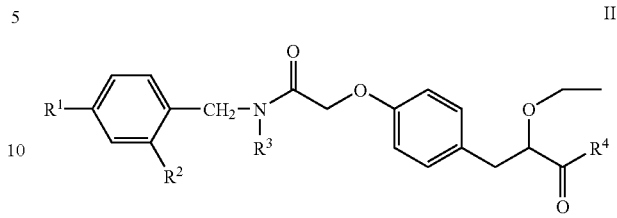

II in which $R^1$, $R^2$ and $R^3$ are as previously defined and $R^4$ represents a protecting group for a carboxylic hydroxy group as described in the standard text "Protective Groups in Organic Synthesis", 3rd Edition (1999) by Greene and Wuts: with a de-protecting agent. The protecting group may also be a resin, such as Wang resin or 2-chlorotrityl chloride resin. Protecting groups may be removed in accordance to techniques which are well known to those skilled in the art. One such protecting group is where $R^4$ represents a $C_{1-6}$alkoxy group for example methoxy or ethoxy or an arylalkoxy group eg benzyloxy, such that $COR^4$ represents an ester. Such esters can be reacted with a de-protecting agent. e.g. a hydrolysing agent, for example lithium hydroxide in a mixture of THF and water, at a temperature in the range of 0-100° C. to give compounds of formula I.

Compounds of formula II may be prepared by reacting the S-enantiomer of a compound of formula III

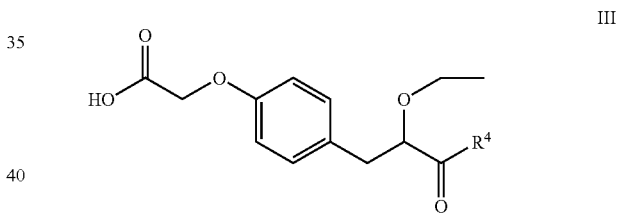

III in which $R^4$ is as previously defined with a compound of formula IV

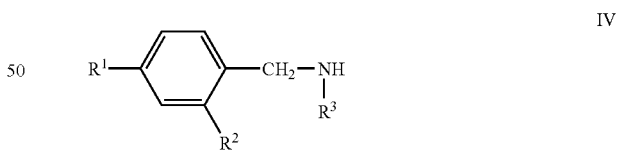

IV in which $R^1$, $R^2$ and $R^3$ are as previously defined in an inert solvent, for example dichloromethane, in the presence of a coupling agent, for example a carbodiimide, eg 1-(3-dimethylaminopropyl)-3-ethylcarbodiimide, and optionally in the presence of a catalyst, for example a basic catalyst, eg 4-dimethylaminopyridine, at a temperature in the range of −25° C. to 150° C.

Compounds of formula III and IV may be prepared by methods described in the Examples or by analogous methods known to those skilled in the art.

Compounds of formula II and III are useful intermediates in the preparation of compounds of formula I and are believed to be novel. Compounds of formula II and II are herein claimed as a further aspect of the present invention. The S-enantiomers of compounds of formula II and III are preferred.

Compounds of formula I may be also prepared by reacting a compound of formula V,

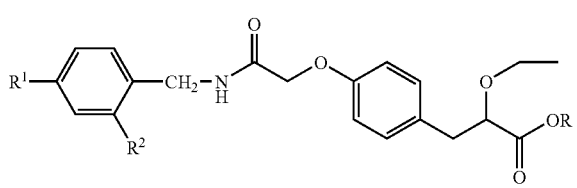

V in which $R^1$ and $R^2$ are as previously defined, R is H or OR represents a protecting group for a carboxylic hydroxy group with a compound of formula VI $R^3X$  VI wherein $R^3$ is as previously defined and X is a leaving group, in the presence of a base in the presence of an inert solvent at a temperature in the range −25° C. to 150° C. and optionally, when OR represents a protecting group, removal of the protecting group.

In particular a compound of formula I may be prepared by reacting a compound of formula VII

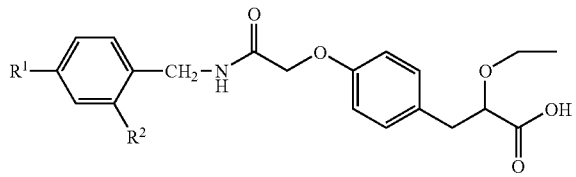

VII in which $R^1$ and $R^2$, are as previously defined with a compound of formula VI $R^3X$  VI wherein $R^3$ is as previously defined and X is a leaving group in the presence of a base in the presence of an inert solvent at a temperature in the range −25° C. to 150° C.

The protecting groups OR and deprotecting agents are described in the standard text "Protective Groups in Organic Synthesis", 3$^{rd}$ Edition (1999) by Greene and Wuts, which is herein, incorporated by reference. Suitable protecting groups include where OR represents a $C_{1-6}$alkoxy group eg methoxy or ethoxy group or an arylalkoxy group eg benzyloxy. In particular, when OR represents a $C_{1-6}$alkoxy group eg ethoxy group or an arylalkoxy group eg benzyloxy, such that COOR represents an ester then such esters may be reacted with a de-protecting agent e.g. a hydrolysing agent, for example lithium hydroxide in a mixture of THF and water, at a temperature in the range of 0-100° C.

Suitable bases include potassium hydroxide, sodium hydroxide, lithium hydroxide, sodium hydride, potassium tert-butoxide, cesium carbonate, potassium carbonate, or sodium carbonate particularly potassium hydroxide.

Suitable inert solvents include dimethyl sulphoxide, N,N-dimethylformamide, N-methylpyrrolidone or toluene or mixtures thereof, particularly dimethyl sulphoxide.

Suitably X represents bromo, chloro, $OSO_2CH_3$, OTosyl, $OSO_2CF_3$, OC(O)OR, OP(O)(OR)$_2$ or $OSO_2OR$. Particularly X is chloro or bromo.

Optionally a phase transfer catalyst may be used for example an alkylammonium salt for example a tetraalkylammonium halide salt eg tetrabutyl ammonium bromide.

Compounds of formula V in which R is H (or compound VII) may be prepared by reacting a compound of formula V

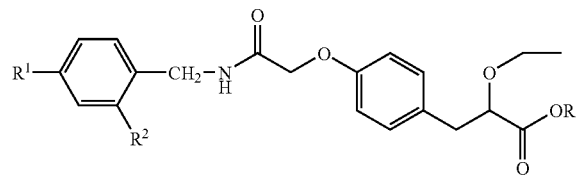

V in which $R^1$ and $R^2$ are as previously defined and OR represents a protecting group for a carboxylic hydroxy group with a de-protecting agent. In particular, OR represents a $C_{1-6}$alkoxy group eg ethoxy group or an arylalkoxy group eg benzyloxy, such that COOR represents an ester. Such esters can be reacted with a de-protecting agent e.g. a hydrolysing agent, for example lithium hydroxide in a mixture of THF and water, at a temperature in the range of 0-100° C.

Compounds of formula V in which OR represents a protecting group for a carboxylic hydroxy group may be prepared by reacting a compound of formula VIII

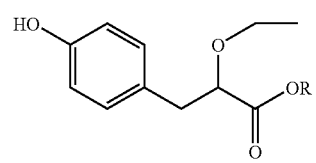

VIII in which OR is as previously defined with a compound of formula IX

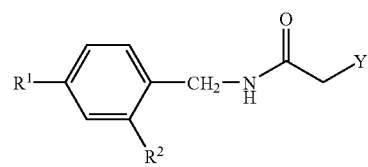

IX in which $R^1$ and $R^2$ are as previously defined and Y represents a leaving group, for example halo, particularly chloro, in an inert solvent, for example acetonitrile or methyl isobutylketone, in the presence of a base, for example potassium carbonate, at a temperature in the range of 0° C. to 150° C.

It is believed that the compounds of formula V in which R is H (compound VII), for example
(2S)-3-[4-(2-{[2-fluoro-4-(trifluoromethyl)benzyl]amino}-2-oxoethoxy)phenyl]-2-ethoxy propanoic acid;
(2S)-3-(4-{2-[4-Chlorobenzylamino]-2-oxoethoxy}phenyl)-2-ethoxypropanoic acid;
(2S)-2-Ethoxy-3-[4-(2-{4-(trifluoromethoxy)benzylamino}-2-oxoethoxy)phenyl]propanoic acid; and
(2S)-2-Ethoxy-3-[4-(2-{4-(trifluoromethyl)benzylamino}-2-oxoethoxy)phenyl]propanoic acid;
are novel and are herein claimed as a further part of the present invention. These compounds have the advantage of being solid and therefore offer an opportunity for purification and isolation during the reaction sequence if desired. These compounds are also modulators of PPAR alpha and/or PPAR gamma and are believed to be useful in treating the indications described herein.

Also claimed herein is a compound of formula V in which OR represents a protecting group for a carboxylic hydroxy group in particular OR represents for example a $C_{1-6}$alkoxy group eg methoxy, ethoxy or propoxy or an arylalkoxy group wherein aryl is phenyl optionally substituted by $C_{1-6}$alkyl, $C_{1-6}$alkoxy or halo, eg benzyloxy, for example a compound of formula X

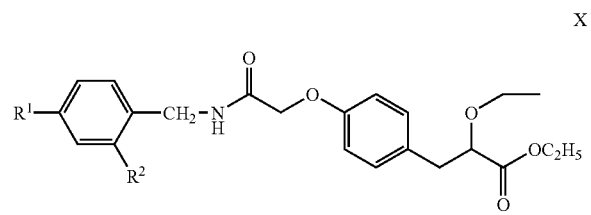

X in which $R^1$ and $R^2$ are as previously defined.

In another aspect the present invention provides a process for preparing a pharmaceutically acceptable salt of the compound of formula I comprising reacting the acid obtained by one of the processes of the present invention with a base, optionally in the presence of a solvent and isolating the salt.

Preferably the compound of formula I prepared by the process is the (2S)-enantiomer.

Similarly the preferred compounds of formulae V and X are: the (2S)-enantiomer.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert solvent" refers to a solvent that does not react with the starting materials, reagents, intermediates or products in a manner that adversely affects the yield of the desired product.

Pharmaceutical Preparations

The compounds of the invention will normally be administered via the oral, parenteral intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

Suitable daily doses of the compounds of the invention in therapeutic treatment of humans are about 0.0001-100 mg/kg body weight, preferably 0.001-10 mg/kg body weight.

Oral formulations are preferred particularly, tablets or capsules which may be formulated by methods known to those, skilled in the art to provide doses of the active compound in the range of 0.5 mg to 500 mg for example 1 mg, 3 mg; 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities.

Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies-causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis. The compounds may be useful in treatment of psoriasis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal particularly a human) in need thereof.

The present invention provides a method of treating or preventing type 2 diabetes comprising the administration of an effective amount of a compound of formula I to a mammal (particularly a human) in need thereof.

The present invention provides a method of treating or preventing atherosclerosis comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes and obesity.

The compounds of the invention may be combined with another therapeutic agent that decreases the ratio of LDL: HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these, include biguanide drugs, for example metformin, phenformin and buformin, insulin (synthetic insulin analogues; amylin) and oral antihyperglycemics (these are divided into prandial glucose regulators and alpha-glucosidase inhibitors). An example, of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt, solvate, solvate of such a salt oil a prodrug thereof, may be administered in association with; another PPAR modulating agent. PPAR modulating agents include but are not limited to a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871', WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to NN622/Ragaglitazar, BMS 298585, WY-14643, clofibrate, fenofibrate, bezafibrate, gemfibrozil and ciprofibrate; GW 9578, ciglitazone, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)-phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl (methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]pyrimidin-5-yl](3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl](3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or holestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 96/05188, WO 96/08484, WO 96/16051, WO 97/33882, WO 98/67449, WO 98/03818, WO 98/38182, WO 99/32478, WO 99/35135, WO 98/40375, WO 99/35.153, WO 99/64409, WO 99/6.4410, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, EP 864 582, EP489423, EP549967, EP573848, EP624593, EP624594, EP624595 and EP624596 and the contents of these patent applications are incorporated herein by reference.

Particular classes of BAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1dioxido-5-phenyl-2,3,4,5-tetrahydro-1,4-benzothiazepin-8-yl β-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl) carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N'-{(R)-α-[N-(2-sulphoethyl) carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5tetrahydro-1,5-benzothiazepine, 1,1-dioxo-3-butyl-3-ethyl-5-phenyl-7-methylthio-8-(N-{(R)-α-[N'-(5-carboxypentyl]carbamoyl) benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-}(R)-1-[N''-(R)-(2-carboxyethyl)carbamoyl]-2-hydroxyethyl{carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N'-{α-[N-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphorylmethyl)carbomoyl] benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-}2-[(hydroxy)(methyl)phosphoryl] ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-}(R)-α-[N'-(2-methylthio-1-carboxyethyl)carbamoyl] benzyl{carbamoylmethoxy)-2,3,4,5-tetrahydro-1,5-benzothiazepine;

1,1-dioxo-3,3-dibutyl-5-phenyl-7-methylthio-8-}N-[(R)-α-(N'-{2-[(methyl)(ethyl)phosphoryl]ethyl}carbamoyl)4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy{-2,3,4,5-tetrahydro-1,5-benzothiazepine;

1,1-dioxo-3,3-dibutyl-5-phenyl-7-methylthio-8-(N-}(R)-α-[(R)-N'-(2-methysulphinyl-1-carboxyethyl)carbamoyl] benzyl{carbamoylmethoxy)-2,3,4,5-tetrahydro-1,5-benzothiazepine;

1,1-dioxo-3,3-dibutyl-5-phenyl-7-methoxy-8-[N-}(R)-α-[N'-(2-sulphoethyl)carbamoyl]-4-hydroxybenzyl{carbamoylmethoxy]-2,3,4,5-tetrahydro-1,5-benzothiazepine;

1,1-dioxo-3,3-dibutyl-5-phenyl-7-methythio-8-(N-}(R)-α-[N-((R)-1-carboxy-2-methylthioethy carbamoy]-4-hydroxybenzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxy-2-(R)-hydroxypropyl)carbamoyl]-4-hydroxybenzyl{carbamoylmethoxy)-2,3,4,5-tetrahydro-1,2,5benzothiadiazepine;

1,1-dioxo-3,3-dibutyl-5-phenyl-7-methylthio-8-(N-}(R)-α-[N-((S)-1-carboxy-2-methylpropyl)carbamoyl]-4-hydroxybenzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxybutyl)carbamoyl]-4-hydroxybenzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxypropyl) carbamoyl] benzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxyethyl)carbamoyl]benzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxy-2-(R)-hydroxyproply)]benzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-(2-sulphoethyl)carbamoyl]-4-hydroxybenzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxyethyl)carbamoyl]-4-hydroxybenzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((R)-1-carboxy-2-methylthioethyl)carbamoyl]benzyl{carbamoylmethoxy)-2,3,4,5-tetrahydro 1,2,5-benzothiadiazepine;

1,1-dioxo-3,3-dibutyl-5-phenyl-7-methylthio-8-(N-}(R)-α-[N-{(S)-1-[N-((S)-2-hydroxy-carboxyetyl) carbamoyl] propyl}carbamoyl]benzyl{carbamoylmethoxy)-2,3,4,5-tetrahydro-1,2,5-benzothiadiazepine;

1,1-dioxo-3,3-dibutyl-5-phenyl-7-methylthio-8-(N-}(R)-α-[N-((S)-1-carboxy-2-methylpropyl)carbamoyl]benzyl{carbamoylmethoxy)-2,3,4,5-tetrahydro-1,2,5-benzothiadiazepine;

1,1-Dioxo-3,3-dibutyl-5-phenyl-7-methylthio-8-(N-}(R)-α-[N-((S)-1-carboxypropyl)carbamoyl]-4-hydroxybenzyl{carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-}N-[1-(R)-2-(S)-1-hydroxy-1-(3,4-dihydroxyphenyl)prop-2-yl]carbamoyl{-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-}(R)-α-[N-(2-(S)-3-(R)-4-(R)-5(R)    -2,3,4,5,6-pentahydroxyhexyl)carbamoyl]-4-hydroxybenzyl{carbamoylmethoxy)-2,3,4,5-tetrahydro-1,2,5-benzothiadiazepine; and 1,1-Dioxo-3,3-dibutyl-5-phenyl-7-methylthio-8-(N-}(R)-α-[N-(2-(S)-3-(R)-4-(R)-5(R)    -2,3,4,5,6-pentahydroxyhexyl)carbamoyl]benzyl}carbamoylmethoxy)-2,3,4,5-tetrahydro -1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a nicotinic acid derivative, including slow release and combination products, for example, nicotinic acid (niacin), acipimox and niceritrol;

a phytosterol compound for example stanols;

probucol;

an omega-3 fatty acid for example Omacor™;

an anti-obesity compound for example orlistat (EP 129,748) and sibutramine (GB 2,184,122 and U.S. Pat. No. 4,929,629);

an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

aspirin;

a Melanin concentrating hormone (MCH) antagonist;

a PDK inhibitor; or modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, enzoylcaptopril, captopril, captopril-cysteine, captopril-glutathione, ceranapril, ceranopril, eronapril, cilazapril, cilazaprilat, delapril, delapril-diacid, enalapril, enalaprilat, enapril, epicaptopril, foroxymithine, fosfenopril, fosenopril, fosenopril sodium, fosinopril; fosinopril sodium, fosinoprilat, fosinoprilic acid, glycopril, hemorphin-4, idrapril, imidapril, indolapril, indolaprilat, libenzapril, lisinopril lyciumin A, lyciumin B, mixanpril, moexpril, moexiprilat, moveltipril, muracein A, muracein B, muracein C, pentopril, perindopril, perindoprilat, pivalopril, pivopril, quinapril, quinapril hydrochloride, quinaprilat, ramipril, rarmprilat; spirapril, spirapril hydrochloride, spiraprilat, spiropril, spiropnl hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore in an additional feature of the invention, there, is provided a method for for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention'there is provided a kit comprising:
a) a compound of formula I, or a pharmaceutically acceptable salt, solvate, solvate of such a salt or a prodrug thereof, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt, solvate, solvate of such a salt or a prodrug thereof, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

| Abbreviations | |
|---|---|
| DMSO | dimethyl sulfoxide |
| THF | tetrahydrofuran |
| Pd/C | palladium on charcoal |
| DMAP | dimethylaminopyridine |
| t | triplet |
| s | singlet |
| d | doublet |
| q | quartet |
| m | multiplet |
| bs | broad singlet |
| dm | doublet of multiplet |
| bt | broad triplet |
| dd | doublet of doublet |

Example 1

(2S)-3-[4-(2-{Butyl[2-fluoro-4-(trifluoromethyl)benzyl]amino}-2-oxoethoxy)phenyl]-2-ethoxy propanoic Acid (i) Ethyl(2S)-3-{4-[2-(benzyloxy)-2-oxoethoxy]phenyl}-2ethoxypropanoate To a solution: of ethyl(2S)-2-ethoxy-3-(4-hydroxyphenyl)propanoate (23.8 g, 100 mmol, prepared as described in WO99/62872) in a cetonitrile (200 mL) was added anhydrous potassium carbonate (31.9 g, 231 mmol) followed by benzyl brompacetate (17.4 mL, 110 mmol) and the reaction mixture was refluxed overnight. The reaction mixture was allowed to cool to room temperature, insoluble salts were filtered off Sand the solution was concentrated in vacuo. The residue was taken up in ethyl acetate (300 mL), and the organic phase was washed with aqueous NaHCO$_3$ (3×100 mL) and brine (1100 mL), dried over anhydrous MgSO$_4$, and concentrated in vacuo. Purification on silica gel with methylene, chloride as the eluent and collection of pure fractions yielded 22.4 g (58%) of a yellow oil.

$^1$H NMR (400; MHz, CDCl$_3$): δ 1.16 (t, 3H), 1.22 (t, 3H), 2.93-2.97 (m, 2H), 3.35 (m, 1H), 3.97 (m, 1H), 4.16 (q, 2H), 4.64 (s, 2H), 5.23 (s, 2H), 6.82 (d, 2H), 7.15 (d, 2H), 7.32-7.39 (m, 5H).

$^{13}$C NMR (100 MHz, CDCl$_3$): δ 14.3, 15.2, 38.6, 60.9, 65.6, 66.3, 67.0, 80.4, 114.6, 128.5, 128.6, 128.7, 130.6, 135.3, 156.7, 169.0, 172.6.

(ii) {4-[(2S)-2,3-Diethoxy-3-oxopropyl] phenoxy}acetic Acid

To a solution of ethyl(2S)-3-{4-[2-(benzyloxy)-2-oxoethoxy]phenyl}-2-ethoxypropanoate (22.33 g, 57.8 mmol) in freshly distilled THF (290 mL) was added Pd/C (10%, 3.1 g) and the reaction mixture was hydrogenated under atmospheric pressure at room temperature overnight. The mixture was filtered through a plug of Celite and the filtrate was concentrated in vacuo to afford 16.6 g (97%) of a light yellow oil.

$^1$H NMR (400 MHz, CDCl$_3$): δ 1.15 (t, 3H), 1.21 (t, 3H), 2.93-2.98 (m, 2H), 3.35(m, 1H), 3.97 (m, 1H), 4.16 (q, 2H), 4.65 (s, 2H), 6.84 (d, 2H), 7.17 (d, 2H), 8.48 (bs, 1H)

$^{13}$C NMR (100 MHz, CDCl$_3$): δ 14.3, 15.1, 38.5, 61.0, 65.1, 66.4, 80.3, 114.6, 130.7, 130.9, 156.4, 172.7, 173.7

(iii) N-Butyl-N-[2-fluoro-4-(trifluoromethyl)benzyl]amine

To a solution of 2-fluoro-4-(trifluoromethyl)benzaldehyde (3.84 g, 20.0 mmol) and n-butylamine (1.46 g, 20.0 mmol) in methanol (100 mL) were added acetic acid (4.6 mL, 80 mmol) and sodium cyanoborohydride (1.51 g, 24.0 mmol) and the solution was stirred at room temperature for 3 days. Water (10 mL) was added and the mixture was concentrated in vacuo. The residue was taken, up in aqueous 1 M KOH (125 mL) and ethyl acetate (100 mL) and the phases were separated. The aqueous phase was extracted with ethyl acetate (2×100 mL) and the combined organic phase was dried over Na$_2$SO$_4$ and concentrated in vacuo. Purification on a prepacked column of silica gel (Isolute® SPE Column, 70 g/150 mL) with ethyl acetate (33-100% gradient) in heptane as the eluent and collection of pure fractions yielded 1.28 g (26%) of a colourless oil of low viscosity.

$^1$H NMR (400 MHz, CDCl$_3$): δ 0.91 (t, 3H), 1.28-1.41 (m, 2H), 1.44-1.55 (m,2H), 2.62 (t, 2H), 3.88 (s, 2H), 7.29 (m, 1H), 7.38 (m, 1H), 7.51 (m, 1H).

$^{13}$C NMR (100 MHz, CDCl$_3$): δ 14.1, 20.6, 32.4, 47.0, 49.3, 112.8 (m), 121.1 (m), 123.5 (q), 130.5-131.6 (m), 130.8 (m), 132.0 (d), 160.8 (d).

(iv) Ethyl(2S)-3-[4-(2-{butyl[2-fluoro-4-(trifluoromethyl)benzyl]amino}-2-oxoethoxy)phenyl]-2-ethoxypropanoate To a solution of N-butyl-N-[2-fluoro-4-(trifluoromethyl)benzyl]amine (0.598 g, 2.40 mmol) and {4-[(2S)-2,3-diethoxy-3-oxopropyl]phenoxy}acetic acid, (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (100 mL) and the organic phase was washed with 2 M HCl (3×75 mL), saturated aqueous NaHCO$_3$ (2×75 mL), and brine (75 mL), dried over Na$_2$SO$_4$, and concentrated in vacuo. Purification on a prepacked column of silica gel (Isolute® SPE Column, 20 g/70 mL) with methanol (0-2% gradient) in methylene chloride as the eluent yielded 0.785 g (74%) of a pale yellowish-white oil.

$^1$H NMR (400 MHz, CDCl$_3$): δ 0.84-0.97 (m, 3H), 1.11-1.19 (m, 3H), 1.19-1.40(m,5H), 1.45-1.65 (m, 2H), 2.90-2.99 (m, 2H), 3.29-3.40 (m, 3H), 3.60 (m, 1H), 3.96 (m, 1H), 4.16 (q, 2H), 4.68 (s, 2H), 4.72 and 4.74 (2s, 2H, rotamers), 6.70 and 6.86 (2d, 2H, rotamers), 7.10 and 7.17 (2d, 2H, rotamers), 7.21-7.40 (m, 3H).

$^{13}$C NMR (100 MHz, CDCl$_3$): δ 13.8, 14.3, 15.2, 20.2, 29.2, 30.9, 38.5, 42.1 (d), 44.6 (d), 46.2, 47.5, 60.9, 66.3, 67.6, 68.3, 80.4, 113.0 (m), 114.3, 114.6, 121.4 (m), 123.3 (q), 128.5 (m), 129.1 (d), 130.6, 130.6, 130.7, 131.0 (d), 131.0-132.2 (m), 156.6, 156.8, 160.3 (4), 160.5 (d), 168.5, 168.6, 172.6. (The number of peaks is larger than the number of carbon atoms due to rotamers.)

(v) (2S)-3-[4-(2-{Butyl[2-fluoro-4-(trifluoromethyl)benzyl]amino}-2-oxoethoxy)phenyl]-2-ethoxypropanoic Acid To a solution of ethyl(2S)-3-[4-(2-}butyl[2-fluoro-4-(trifluoromethyl)benzyl]amino{-2-oxoethoxy)phenyl]-2-ethoxypropanoate (0.748 g, 1.42 mmol) in acetonitrile (70 mL) was added aqueous 0.10 M LiOH (35 mL) and the reaction mixture was stirred at room temperature overnight. After neutralisation with 5% HCl; the solvent volume was reduced in vacuo and the remaining aqueous phase was acidified with 5% HCl and extracted with ethyl acetate (3×100 mL). The combined organic phase was washed with brine (100 mL), dried over Na$_2$SO$_4$, and concentrated in vacuo to afford 0.688 g (97%) of a pale yellow oil.

$^1$H NMR (400 MHz, CDCl$_3$): δ 0.84-0.96 (m, 3H), 1.16 (t, 3H), 1.21-1.40 (m, 2H), 1.45-1.66(m, 2H), 2.88-3.11 (m, 2H), 3.29-3.46 (m, 3H), 3.61 (m, 1H), 4.02 (m, 1H), 4.69 (s, 2H), 4.73 and 4.75 (2s, 2H, rotamers), 6.70 an 6.86 (2d, 2H, rotamers), 7.12 and 7.18 (2d, 2H, rotamers), 7.22-7.41 (m, 3H), 8.66 (bs, 1H).

$^{13}$C NMR (100 MHz, CDCl$_3$): δ 13.8, 15.1, 20.1, 29.2, 30.8, 38.0, 42.2 (d), 44.6 (d), 46.3, 47.5, 66.8, 67.4, 68.1, 79.8, 113.0 (m), 114.4, 114.6, 121.4 (m), 123.3 (q), 128.3 (m), 129.1 (d), 130.2, 130.7, 130.8, 131.0 (d), 131.0-132.2 (m), 156.7, 156.9, 160.3 (d), 160.5 (d), 168.8, 168.9, 175.6. (The number of peaks is larger than the number of carbon atoms due to rotamers.)

Example 2

(2S)-3-(4-{2-[(4-Chlorobenzyl)(ethyl)amino]-2-oxoethoxy}phenyl)-2-ethoxypropanoic Acid (i) Ethyl(2S)-3-(4-{2-[(4-chlorobenzyl)(ethyl)amino]-2-oxoethoxy{phenyl)-2-ethoxypropanoate To a solution of N-(4-chlorobenzyl)-N-ethylamine (0.150 g, 0.88 mmol) and {4-[(2S)-2,3-diethoxy-3-oxopropyl] phenoxy}acetic acid (0.270 g, 0.91 mmol) in methylene chloride (10 mL) were added N,N-diisopropylethylamine (0.34 mL, 1.9 mmol) and O-(benzotriazol-1-yl)-N,N,N',N'-tetramethyluronium tetrafluoroborate (0.320 g, 1.00 mmol) and the reaction mixture was stirred at room temperature overnight. The resulting solution was diluted with methylene chloride (40 mL) and the organic phase was washed with 5% HCl (50 mL), saturated aqueous NaHCO$_3$ (50 mL), and brine (50 mL), dried over Na$_2$SO$_4$, and concentrated in vacuo. Purification on a prepacked column of silica gel (Isolut® SPE Column, 50 g/150 mL) with methylene chloride/ethyl acetate 10:1 as the eluent yielded 0.4 g (61%) of a colurless oil.

$^1$HMR (500 MHz, CDCl$_3$): δ 1.05-1.24 (m, 9H), 2.88-3.00 (m, 2H), 3.28-3.42 (m, 3H), 3.60 (m, 1H), 3.96 (m, 1H), 4.12-4.20 (m, 2H), 4.56 and 4.58 (2s, 2H, rotamers), 4.64 and 4.73 (2s, 2H, rotamers), 6.75 and 6.88 (2d, 2H, rotamers), 7.09-7.20 (m, 4H), 7.24 and 7.30 (2d, 2H, rotamers).

(ii) (2S)-3-(4-{2-[(4-Chlorobenzyl)(ethyl)amino]-2-oxoethoxy{phenyl)-2-ethoxypropanoic Acid To a solution of ethyl(2S)-3-(4-{2-[(4-chlorobenzyl)(ethyl)amino]-2-oxoethoxy}phenyl)-2-ethoxypropanoate (0.240 g, 0.54 mmol) in THF (30 mL) was added aqueous 0.10 M LiOH (15 mL) and the solution was stirred at room temperature overnight. After neutralisation with 5% HCl, the solvent volume was reduced in vacuo and the remaining aqueous phase was acidified with 5% HCl and extracted with methylene chloride (2×50 mL). The combined organic phase was washed with brine (50 mL), dried over Na$_2$SO$_4$, and concentrated in vacuo. Purification on a prepacked column of silica gel (Isolute® SPE Column, 2 g/15 mL) with ethyl acetate as the eluent afforded 0.13 g (61%) of a pale yellow oil.

$^1$H NMR (500 MHz, CDCl$_3$): δ 1.05-1.21 (m, 6H), 2.94 (m, 1H), 3.04 (m, 1H), 3.30-3.45 (m, 3H), 3.61 (m, 1H), 4.01 (m, 1H), 4.57 and 4.58 (2s, 2H, rotamers), 4.66 and 4.73 (2s, 2H, rotamers), 6.74 and 6.87 (2d, 2H, rotamers), 7.10-7.20 (m, 4H), 7.24 and 7.30 (d, 2H, rotamers), 7.98 (bs, 1H).

$^{13}$C NMR (100 MHz, CDCl$_3$): δ 12.3, 13.9, 15.1, 38.0, 41.2, 41.5, 47.6, 49.8, 66.7, 67.4, 68.0, 79.8, 114.5, 114.6, 128.3, 128.8, 129.1, 129.5, 130.2, 130.7, 133.3, 133.6, 135.0, 135.7, 156.7, 156.9, 168.4, 168.4, 175.5. (The number of peaks is larger than the number of carbon atoms due to rotamers.)

Example 3

(2S)-2-Ethoxy-3-[4-(2-{ethyl[4-(trifluoromethoxy)benzyl]amino{-2-oxoethoxyphenyl]propanoic Acid (i) N-[4-(Trifluoromethoxy)benzyl]acetamide To a solution of 4-(trifluoromethoxy)benzylamine (3.46 g, 57.6 mmol) in DMF (75 mL) and acetic acid (10.0 g, 52.3 mmol) at −10° C. were added O-(benzotriazol-1-yl)-N,N,N',N'-tetramethyluronium tetrafluoroborate (20.2 g, 62.8 mmol) and N,N-diisopropylethylamine (20.0 mL, 115 mmol) and the reaction mixture was stirred at room temperature overnight. Ethyl acetate (200 mL) was added and the organic phase was washed with water (100 mL), 0.25 M NaOH (100 mL), saturated aqueous NaHCO$_3$ (100 mL), water (100 mL), 0.5 M HCl (100 mL), and water (100 mL), dried over MgSO$_4$, and concentrated in vacuo to afford 11.2 g (92%) of a colourless oil.

$^1$H NMR (600 MHz, CDCl$_3$): δ 2.03 (s, 3H), 4.43 (d, 2H), 5.83 (bs, 1H), 7.17 (d,2H), 7.31 (d, 2H).

$^{13}$C NMR (125 MHz, CDCl$_3$): δ 22.9, 42.8, 120.5 (q), 121.1, 129.0, 137.3, 148.4, 170.6.

(ii) N-ethyl-N-[4-(Trifluoromethoxy)benzyl]amine

N-[4-(Trifluoromethoxy)benzyl]acetamide (10.4 g, 44.6 mmol) was dissolved in THF (100 mL) and cooled to −10° C. Borane (56 mL of a 2 M solution of the dimethylsulfide complex in diethyl ether) was added and the reaction mixture was stirred at −10° C. for 15 minuters and was then allowed to warm to room temperature. The reaction mixture was refluxed overnight and was then allowed to cool to room temperature. The reaction was quenched by careful addition of 10% HCl (30 mL) at 0° C. and the mixture was stirred at room temperature overnight and then concentrated in, vacuo. The residue was taken up in water (200 mL) and diethyl ether (200 mL) and the phases were separated. Concentration in vacuo of the diethyl ether phase afforded 1.9 g (21%) of the title compound as a colourless oil.

$^1$H NMR (300, MHz, CDCl$_3$): δ 1.28 (t, 3H), 2.72 (q, 2H), 3.83 (s, 2H), 3.86 (bs, 1H), 7.18 (d, 2H), 7.40 (d, 2H).

(iii) Ethyl(2S)-2-ethoxy-3-[4-(2-{ethyl[4-(trifluoromethoxy)benzyl]amino}-2-oxoethoxy)phenyl]propanoate To a solution of N-ethyl-N-[4-(trifluoromethoxy)benzyl]amine (0.438 g, 2.00 mmol) and {4-[(2S)-2,3-diethoxy-3-oxopropyl]phenoxy{acetic acid (0.593 g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (40 mL) and the organic phase was washed with 5% HCl (50 mL), saturated aqueous NaHCO$_3$ (50 mL), and brine (50 mL), dried over Na$_2$SO$_4$, and concentrated in vacuo. Purification on a prepacked column of silica gel (Isolute® SPE Column, 50 g/150 mL) with methylene chloride/ethyl acetate 10:1 as the eluent yielded 0.57 g (58%) of a colourless oil.

$^1$H NMR (500 MHz, CDCl$_3$): δ 1.08-1.28 (m, 9H), 2.88-3.00 (m, 2H), 3.28-3.44 (m, 3H), 3.60 (m, 1H), 3.96 (m, 1H), 4.12-4.20 (m, 2H), 4.60 and 4.62 (2s, 2H, rotamers), 4.66 and 4.74 (2s, 2H, rotamers), 6.74 and 6.89 (2d, 2H, rotamers), 7.08-7.27 (m, 6H).

$^{13}$C NMR (100 MHz, CDCl$_3$): δ 12.4, 14.0, 14.4, 15.2, 38.6, 41.1, 41.5, 47.5, 49.7, 61.0, 66.3, 67.7, 68.3, 80.4, 114.5, 114.6, 121.2, 121.5, 128.3, 129.5, 130.6, 130.7, 130.7, 135.6, 136.1, 148.6, 156.9, 168.1, 168.2, 172.6. (The number of peaks is larger than the number of carbons due to rotamers. Trifluorinated carbon not reported.)

(iv) (2S)-2-Ethoxy-3-[4-(2-{ethyl[4-(trifluoromethoxy)benzyl]amino}-2-oxoethoxy)phenyl] Acid To a solution of ethyl(2S)-2-ethoxy-3-[4-(2-{ethyl[4-(trifluoromethoxy)benzyl]amino{-2-oxoethoxy)phenyl]propanoate (0.560 g, 1.13 mmol) in THF (50 mL) was added aqueous 0.10 M LiOH (25 mL) and the solution was stirred at room temperature overnight. After neutralisation with 5% HCl, the solvent volume was reduced in vacuo and the remaining aqueous phase was acidified with 5% HCl and extracted with ethyl acetate (2×50 mL). The combined organic phase was washed with brine (50 mL), dried over Na$_2$SO$_4$, and concentrated in vacuo. Purification on a prepacked column of silica gel (Isolute® SPE Column, 10 g/70 mL) with ethyl acetate as the eluent afforded 0.457 g (87%) of a colourless oil.

$^1$H NMR (500 MHz, CDCl$_3$): δ 1.08-1.23 (m, 6H), 2.96 (m, 1H), 3.08 (m, 1H), 3.33-3.43 (m, 2H), 3.48 (m, 1H), 3.59 (m, 1H), 4.05 (m, 1H), 4.60 and 4.62 (2s, 2H, rotamers), 4.67 and 4.75 (2s, 2H, rotamers), 6.75 and 6.89 (2d, 2H, rotamers), 7.09-7.27 (m, 6H).

$^{13}$C NMR (100 MHz, CDCl$_3$): δ 12.4, 14.0, 15.2, 37.8, 41.2, 41.6, 47.5, 49.7, 67.0, 67.6, 68.2, 79.8, 114.6, 114.8, 121.2, 121.5, 128.3, 129.5, 129.9, 130.8, 130.8, 135.4, 136.0, 148.7, 148.8, 156.9, 157.0, 168.3, 168.3, 174.2. (The number of peaks is larger than the number of carbons due to rotamers. Trifluorinated carbon not reported.)

Example 4

(2S)-2-Ethoxy-3-[4-(2-{ethyl[4-(trifluoromethyl)benzyl]amino}-2-oxoethoxy)phenyl]propanoic Acid

(i) Ethyl(2S)-2-ethoxy-3-[4-(2-{ethyl[4-(trifluoromethyl)benzyl]amino{-2-oxoethoxy) phenyl]propanoate To a solution of N-ethyl-N-[4-(trifluoromethyl)benzyl]amine (0.213 g, 1.05 mmol) and {4-[(2S)-2,3-diethoxy-3-oxopropyl]phenoxy}acetic acid (0.296 g, 1.00 mmol) in methylene chloride (10 mL) were added N,N-diisopropylethylamine (0.40 mL, 2.3 mmol) and O-(benzotriazol-1-yl)-N,N,N',N'-tetramethyluronium tetrafluoroborate (0.337 g, 1.05 mmol) and the reaction mixture was stirred at room temperature overnight. The resulting solution was diluted with methylene chloride (90 mL) and the organic phase was washed with 5% HCl (2×50 mL), saturated aqueous NaHCO$_3$ (2×50' mL), and brine: (5 mL), dried over Na$_2$SO$_4$, and concentrated in vacuo. Purification on a prepacked column of silica gel (Isolute® SPE Column, 50 g/150 mL) with methanol (0-1% gradient) in methylene chloride as the eluent yielded. 0.339 g (70%) of a colourless oil.

$^1$H NMR (400 MHz, CDCl$_3$): δ 1.06-1.24 (m, 9H), 2.88-3.00 (m, 2H), 3.28-3.44 (m, 3H), 3.59 (m, 1H), 3.96 (m, 1H), 4.10-4.19 (m, 2H), 4.64, 4.67, and 4.74 (3s, 4H, rotamers), 6.71 and 6.88 (2d, 2H, rotamers), 7.10 and 7.17 (2d, 2H, rotamers), 7.30 (d, 2H), 7.52 and 7.57 (2d, 2H, rotamers).

$^{13}$C NMR (100 MHz, CDCl$_3$): δ 12.3, 13.9, 14.3, 15.1, 38.5, 41.2, 41.7, 47.8, 49.9, 60.8, 66.2, 67.6, 68.2, 80.3, 114.4, 114.5, 125.5 (m), 125.8 (m), 127.1, 128.2, 129.2-130.6 (m), 130.5, 130.6, 130.6, 141.0, 141.5, 156.6, 156.8, 168.1, 168.2, 172.5. (The number of peaks is larger than the number of carbon atoms due to rotamers. Trifluorinated carbon not reported.)

(ii) (2S)-2-Ethoxy-3-[4-(2-{ethyl[4-(trifluoromethyl)benzyl]amino{-2-oxoethoxy)phenyl]propanoic Acid To a solution of ethyl(2S)-2-ethoxy-3-[4-(2-{ethyl[4-(trifluoromethyl)benzyl]amino}-2-oxoethoxy)phenyl]propanoate ((0.308 g, 0.64 mmol) in acetonitrile (32 mL) was added aqueous 0.10 M LiOH (16 mL) and the solution was stirred at room temperature overnight. After neutralisation with 5% HCl, the solvent volume was reduced in vacuo and the remaining aqueous phase was diluted with water and aqueous 0.10 M LiOH (to a total volume of 100 mL, pH~10) and washed with diethyl ether (2×100 mL). The aqueous phase was acidified with 5% HCl and extracted with ethyl acetate (3×100 mL). The combined organic phase was washed with 5% HCl (100 mL) and brine (100 mL), dried over Na$_2$SO$_4$, and concentrated in vacuo to afford 0.279 g (96%) of a colourless oil.

$^1$H NMR (400 MHz, CDCl$_3$): δ 1.08-1.24 (m, 6H), 2.88-3.12 (m, 2H), 3.34-3.47 (m, 3H), 3.61 (m, 1H), 4.02 (m, 1H), 4.66, 4.67, 4.69, and 4.76 (4s, 4H, rotamers), 6.72 and 6.89 (2d, 2H, rotamers), 7.12 and 7.19 (2d, 2H, rotamers), 7.32 (d, 2H), 7.53 and 7.58 (2d, 2H, rotamers), 8.08 (bs, 1H).

$^{13}$C NMR (100 MHz, CDCl$_3$): δ 12.3, 13.9, 15.1, 38.0, 41.4, 41.9, 48.0, 50.1, 66.8, 67.5, 68.1, 79.8, 114.5, 114.7, 125.6 (m), 125.9 (m), 127.2, 128.2, 129.2-130.6 (m), 130, 130.7, 130.8, 140.8, 41.3, 156.7, 156.9, 168.6, 168.6, 175.5. (The number of peaks is larger than the number of carbon atoms due to rotamers. Trifluorinated carbon not reported.)

Example 5

(2S)-3-[4-(2-{Butyl[4-(trifluoromethyl)benzyl]amino{-2-oxoethoxy)phenyl]-2-ethoxypropanoic Acid

(i) Ethyl(2S)-3-[4-(2-}butyl[4-(trifluoromethyl)benzyl]amino{-2-oxoethoxy)phenyl]-2-ethoxypropanoate To a solution of N-butyl-N-[4-(trifluoromethyl)benzyl]amine (0.486 g, 2.10 mmol) and {4-[(2S)-2,3-diethoxy-3-oxopropyl]phenoxy}acetic acid (0.593-g, 2.00 mmol) in methylene chloride (20 mL) were added N,N-diisopropylethylamine (0.80 mL, 4.6 mmol) and O-(benzotriazol-1-yl)-N,N,N',N'-tetramethyluronium tetrafluoroborate (0.674 g, 2.10 mmol) and the reaction mixture was stirred at room temperature overnight. The resulting solution was diluted with methylene chloride (80 mL) and the organic phase was washed with 5% HCl (3×50 mL), saturated aqueous NaHCO$_3$ (2×50 mL), and brine (50 mL), dried over Na$_2$SO$_4$, and concentrated in vacuo. Purification on a prepacked column of silica gel (Isolute® SPE Column, 70 g/150 mL) with methanol (0-1% gradient) in methylene chloride as the eluent and collection of pure fractions yielded 0.355 g (35%) of a colourless oil.

$^1$H NMR (400 MHz, CDCl$_3$): δ 0.82-0.93 (m, 3H), 1.09-1.17 (m, 3H), 1.20 (t, 3H), 1.22-1.38 (m, 2H), 1.44-1.61 (m, 2H), 2.87-3.00 (m, 2H), 3.25-3.39 (m, 3H), 3.59 (m, 1H), 3.96 (m, 1H), 4.08-4.18 (m, 2H), 4.64, 4.68, and 4.75 (3s, 4H, rotamers), 6.72 and 6.87 (2d, 2H, rotamers), 7.10 and 7.17 (2d, 2H, rotamers), 7.29 (d, 2H), 7.51 and 7.56 (2d, 2H, rotamers).

$^{13}$C NMR (100 MHz, CDCl$_3$): δ 13.5, 14.0, 14.9, 19.9, 29.0, 30.5, 38.3, 45.9, 46.7, 48.1, 50.1, 60.6, 66.0, 67.3, 67.9, 80.1, 114.2, 114.3, 125.3 (m), 125.6 (m), 126.9, 127.9, 128.8-130.5 (m), 130.2, 130.3, 130.4, 141.0, 141.4, 156.5, 156.7, 168.1, 172.2. (The number of peaks is larger than the number of carbon atoms due to rotamers. Trifluorinated carbon not reported.)

(ii) (2S)-3-[4-(2-{Butyl[4-(trifluoromethyl)benzyl]amino{-2-oxoethoxy)phenyl]-2-ethoxy Propanoic Acid To a solution of ethyl(2S)-3-[4-(2-}butyl[4-(trifluoromethyl)benzyl]amino{-2-oxoethoxy) phenyl]-2-ethoxypropanoate (0.311 g, 0.61 mmol) in acetonitrile (30 mL) was added aqueous 0.10 M LiOH. (15 mL) and the solution was stirred at room temperature overnight. After acidification with 5% HCl, the mixture was extracted with ethyl acetate (3×100 mL) and the combined organic phase was washed with 5% HCl (100 mL) and brine (100, mL), dried over Na$_2$SO$_4$, and concentrated in vacuo to afford 0.232 g (79%) of a colourless oil.

$^1$H NMR (400 MHz, CDCl$_3$): δ 0.84-0.94 (m, 3H), 1.10-1.19 (m, 3H), 1.20-1.36 (m, 2H), 1.46-1.62 (m, 2H), 2.87-3.10 (m, 2H), 3.25-3.45 (m, 2H), 3.61 (m, 1H), 4.01 (m, 1H), 4.66, 4.69 and 4.76 (3s, 4H, rotamers), 6.72 and 6.88 (2d, 2H, rotamers), 7.12 and 7.19 (2d, 2H, rotamers), 7.30 (d, 2h), 7.53 and 7.59 (2d, 2H, rotamers), 8.27 (bs, 1H).

$^{13}$C NMR (100 MHz, CDCl$_3$): δ 13.8, 15.1, 20.1, 29.2, 30.7, 38.0, 46.3, 47.0, 48.4, 50.4, 66.7, 67.4, 68.1, 79.8, 114.5, 114.6, 125.6 (m), 125.9 (m), 127.1, 128.2, 129.2-130.5 (m), 130.2, 130.7, 130.8, 140.8, 141.2, 156.7, 156.9, 168.8, 175.6. (The number of peaks is larger than the number of carbon atoms due to rotamers. Trifluorinated carbon not reported.)

Biological Activity

The compounds of the invention were tested in the assays described in WO03/051821.

The compounds of formula I have an EC$_{50}$ of less than 0.1 μmol/l for PPARα and particular compounds have an EC$_{50}$ of less than 0.01 μmol/l. Additionally in particular compounds the ratio of the EC$_{50}$ (PPARγ) EC$_{50}$ (PPARα) is greater than 150:1. It is believed that this ratio is important with respect to the pharmacological activity of the compounds and to their therapeutic profile.

In addition the compounds of the present invention exhibit improved DMPK (Drug Metabolism and Pharmacokinetic) properties for example they exhibit improved metabolic stability in vitro. The compounds also have a promising toxicological profile.

The EC$_{50}$s of the Examples for human PPAR alpha are:
Example 1 0.001 μmol/l;
Example 2 0.003 μmol/l;
Example 3 0.003 μmol/l;
Example 4 0.005 μmol/l; and
Example 5 0.003 μmol/l

The invention claimed is:

1. The S enantiomer of a compound of formula I

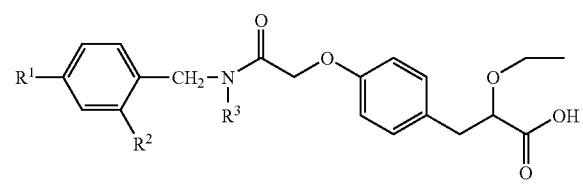

wherein R$^1$ represents chloro, trifluoromethyl or trifluoromethoxy, R$^2$ represents H or fluoro and R$^3$ represents a C$_{2-4}$alkyl group as well as pharmaceutically acceptable salts thereof.

2. (2S)-3-[4-(2-{Butyl[2-fluoro-4-(trifluoromethyl)benzyl] amino }-2-oxoethoxy)phenyl]-2ethoxy propanoic acid and pharmaceutically acceptable salts thereof.

3. (2S)-3-(4-{2-[(4Chlorobenzyl)(ethyl)amino]-2-oxoethoxy{ phenyl)-2-ethoxypropanoic acid and pharmaceutically acceptable salts thereof.

4. (2S)-2-Ethoxy-3-[4-(2-{ethyl[4(trifluoromethoxy)benzyl]amino }-2-oxoethoxy)phenyl]-propanoic acid and pharmaceutically acceptable salts thereof.

5. (2S)-2-Ethoxy-3-[4-(2-{ethyl[4-(trifluommethyl)benzyl]amino}-2-oxoethoxy)phenyl]propanoic acid and pharmaceutically acceptable salts thereof.

6. (2S)-3-[4-(2-{Butyl[4-trifluoromethyl)benzyl]amino{-2-oxoethoxy)phenyl]-2-ethoxypropanoic acid and pharmaceutically acceptable salts thereof.

7. A pharmaceutical formulation comprising a compound according to claim 1 in admixture with pharmaceutically acceptable adjuvants, diluents and/or carriers.

8. A process for the preparation of a compound of formula I

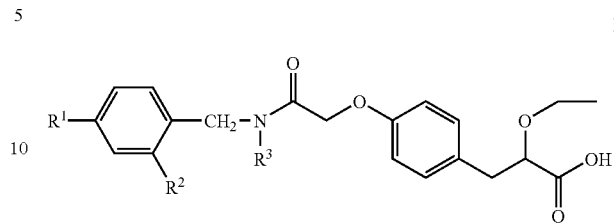

wherein R$^1$ represents chloro, trifluoromethy, or trifluoromethoxy, R$^2$ represents H or fluoro and R$^3$ represents a C$_{2-4}$ alkyl group comprising reacting the S-enantiomer of a compound of formula II

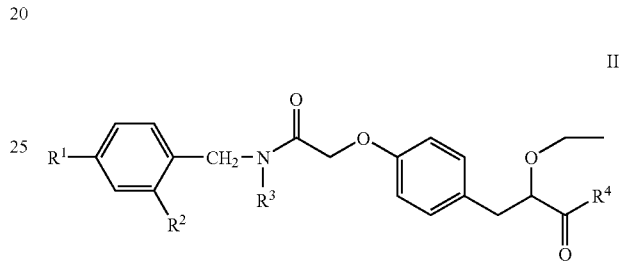

in which R$^1$, R$^2$ and R$^3$ are as previously defined and R$^4$ represents a protecting group for a carboxylic hydroxy group with a de-protecting agent.

9. A compound of formula II

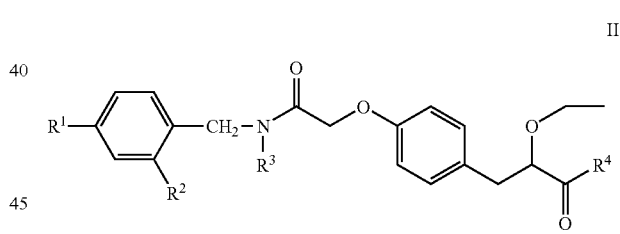

wherein R$^1$ represents chloro, trifluoromethyl or trifluoromethoxy, R$^2$ represents H or fluoro, R$^3$ represents a C$_{2-6}$alkyl group and R$^4$ represents a protecting group for a carboxylic hydroxy group.

10. A process for the preparation of a compound of formula I comprising reacting a compound of formula V,

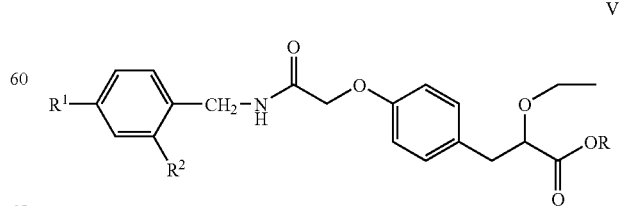

in which R¹ represents chloro, trifluoromethyl or trifluoromethoxy, R² represents H or fluoro, and R is H or OR represents a protecting group for a carboxylic hydroxy group with a compound of formula VI $$R^3X \qquad VI$$

wherein R³ represents a $C_{2-4}$ alkyl group and X is a leaving group, in the presence of a base in the presence of an inert solvent at a temperature in the range −25° C. to 150° C. and optionally, when OR represents a protecting group, removal of the protecting group.

11. A compound of formula V selected from (2S)-3-[4-(2-}[2-fluoro-4-(trifluoromethyl)benzyl]amino)-2-oxoethoxy)phenyl]-2-ethoxy propanic acid;
(2S)-3-(4-{2-[4-Chlorobenzylamino]-2-oxoethoxy{phenyl)-2-ethoxypropanoic acid;
(2S)-2-Ethoxy-3-[4-(2-{4-(trifluoromethoxy)benzylamino)-2-oxoethoxy)phenyl]propanoic acid; and
(2S)-2-Ethoxy-3-[4-(2-{4-(trifluoromethyl)benzylamino)-2-oxoethoxy)phenyl]propanoic acid.

12. A pharmaceutical composition comprising a compound as claimed in claim 1 combined with another PPAR modulating agent.

13. A pharmaceutical composition comprising a compound as claimed in claim 1 combined with a cholesterol-lowering agent.

14. A pharmaceutical composition comprising a compound as claimed in claim 1 combined with a HMG-CoA reductase inhibitor.

15. A pharmaceutical composition comprising a compound as claimed in claim 1 combined with atorvastatin or a pharmaceutically acceptable salt thereof.

16. A pharmaceutical composition comprisinig a compound as claimed in claim 1 combined with rosuvastatin or a pharmaceutically acceptable salt thereof.

17. A pharmaceutical composition comprising a compound as claimed in claim 1 combined with an IBAT inhibitor.

18. A pharmaceutical composition according to claim 17 wherein the IBAT inhibitor is selected from one of:
1,1 dioxo3,3-dibutyl5phenyl7methylthio-8-(N-}(R)-1'-phenyl-1'[N'(carboxymethyl) carbamoyl]methyl{carbamoylmethoxy)-2,3,4.5tetrahydro-1, 5-benzothiazepine;
1 dioxo3,3-dibutyl-5 phenyl7methylthio-8(N-}(R)-α-[N'-(carboxymethyl)carbamoyl]-4-hydroxybenzyl{carbamoymethoxy)-2,3,4,5-tetrahydro-1, 5-benzothiazepine;
1,1 dioxo-3,3-dibutyl-5-phenyl-7-methylthio-8-(N-}(R)-1'-phenyl 1'-[N'-(2-sulphoethyl)carbamoyl]methyl{carbamoylmethoxy)-2,3,4,5-tetrahydro -1,5-benzothiazepine;
1,1 dioxo3,3butyl-5-phenyl-7-methylthio-8-(N-}(R)-α-[N'-(2-sulphoethyl) carbamoyl]-4hydroxybenzy{carbamoylmethoxy)-2,3,4,5-tetrahydro-1,5-benzothiazepine
1,1-dioxo-3-butyl-3-ethyl-5-phenyl-7-methylthio-8-(N-}(R)-α-[N'-(2-sulphoethyl) carbamoy]-4-hydroxybenzyl{carbamoylmethoxy)-2,3,4,5-tetraht-dro-1,5-benzothiazepine;
1,1-dixo-3-butyl-3-ethyl-5-phenyl-7-methylthio-8-(N'-(2-sulphoethyl)carbamoyl]-4-hydroxybenzyl}cambamoylmethoxy)-2,3,4,5-tetrahydro-1,5-benzothiazepine;
1,1-dioxo-3-butyl-3-ethyl-5-phenyl-7-methlthio-8-(N-{(R)-α-[N'-(2-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methylthio-8-(N-{(R)-α-[N'-(2-carboxyethyl)carbamoy]-4-hydroxybenzyl}carbamoylmethoxy)-2,3,4,5-tetrahydro-1,5-benzothiazepine;
1,1-dioxo-3-butyl-3-ethyl-5-phenyl-7-methylthio-8-(N-{(R)-α-[N'-(5-carboxyphenyl)carbonoyl]benzyl}carbarnoylmethoxy)-2,3,4,5-tetrahydro-1,5-benzothiazepone;
1,1-dioxo-3,3-dibuytl-5-phenyl-7-methylthio-8-(N-{(R)-α-[N'-(2-carboxyethyl)carbarnoyl]benzyl}carbornoylmethoxy)-2,3,4,5-tetrahydro-1,5-benzothiazepine;
1,1-dioxo-3,3-dibutyl-5-phenyl-7-methylthio-8-(N'-{α-[N'-(2-sulphoethyl) carbarnoyl]-2-fluorobenzyl}carbarnoylmethoxy)-2,3,4,5-tetrahydro-1,5-benzothiazepine;
1,1-dioxo-3-butyl-3-ethyl-5-phenyl-7-methylthio-8-(N-[(R)-α-[N'-(R)-(2-hydroxy-1-carboxyethyl)carbornoyl]benzyl{carbarnoylmethoxy)-2,3,4,5-tetrahydro-1,5-benzothiazepine;
1,1-dioxo-3,3-dibutyl-5-phenyl-7-methylthio-8-(N-}(R)-α-[N'-(R)-(2-hydroxy-1-carboxyethyl)carbamoyl]benzyl{carbamoylmethoxy)-2,3,4,5-tetrahydro-1,5-benzothiazepine;
1,1-dioxo-3,3-dibutyl-5-phenyl-7-methylthio-8-}N-[(R)-α-(N'-{(R)-1-[N"-(R) -(2-hydroxy-1-carboxyethyl)carbamoyl]-2-hydroxyethyl}carbamoyl)benzyl]carbamoylmethoxy{-2,3,4,5-tetrahydro-1,5-benzothiazepine;
1,1-dioxo-3-butyl-3-ethyl-5-phenyl-7-methylthio-8-(N-}α-[N'-(carboxymethyl)carbamoy]benzyl{carbamoylmethoxy)-2,3,4,5-tetrahydro-1,5-benzothiazepine;
1,1-dioxo-3-butyl-3-ethyl-5-phenyl-7-methylyhio-8-(N-}α-N'-((ethoxy)(methyl)phosphoryl -methyl)carbamoyl]benzyl{carbamoylmethoxy)-2,3,4,5-tetrahydro-1, 5-benzothiazepine;
1,1-dioxo-3-butyl-3-ethyl-5-phenyl-7-methylthio-8-}N-[(R)-α-(N'-{2-[(hydroxy)methyl)phosphoryl]ethyl{carbamoylmethoxy}-2,3,4,5-tetrahydro -1,5-benzothiazepine;
1,1-dioxo-3,3-dibutyl-5-phenyl-7-methylthio-8-(N-{(R)-α-[N'-(2-methylthio-1-carboxyethyl)carbamoy]benzyl}carbamoylmethoxy)-2,3,4,5-tetrahydro-1,5-benzothiazepine;
1,1-dioxo-3,3-dibutyl-5-phenyl-7-methylyhio-8-{N-[(R)-α-N'-{2-[(methyl)(ethyl) phosphoryl]ethyl}carbamoyl)-4-hydroxybenzyl]carbamoylmethoxy{-2,3,4,5-tetrahydro-1,5benzothiazepine;
1,1-dioxo-3,3-dibutyl-5-phenyl-7-methythio-8-}N-[(R)-α-(N'-{2-[(methyl)(hydroxy)phosphory]ethyl{carbomoyl)-4-hydroxybenzyl]carbamoylmethoxy}-2,3,4,5-tetrahydro-1,5-benzothiazepine;
1,1-dioxo-3,3-dibutyl-5-phenyl-7-methylthio-8-(N-{(R)-N'-(2-methylsulphinyl-1-carboxyethyl)carbamoyl]benzyl}carbamoylmethoxy)-2,3,4,5-tetrahydro-1,5-benzothiazepine;
1,1-dioxo-3,3-dibutyl-5-phenyl-7-methoxy-8-[N-{(R)-α[N'-(2-sulphoethyl)carbamoyl]-4-hydroxybenzyl}carbamoylmethoxyl]-2,3,4,5-tetrahydro-1,5-benzothiazepine;
1,1-dioxo-3,3-dibutyl-5-phenyl-7-methylythio-8-(N-{(R)-α-[N'-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoy]-4-hydroxbenzyl}carbamoylmethoxy)-2,3,4,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahhydro-1,2,5-benzothiadiazepine;

1,1-dioxo-3,3-dibutyl-5-phenyl-7-methylthio-8-(N-{(R)-α-[N-((S)-1carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5phenyl-7-methylthio-8-N-{(R)-α-[N-((S)-1-carboxypropyl) carbamoyl]benzyl}carbamoylmethoxy)-2,3,4,5-tetrahydro-1,2,5-benzothiazepine;

1,1-dioxo-3,3-dibutyl-5-phenyl-7-methylthio-8-(N-{(R)-α-[N-((S)-1-carboxyethyl) carbamoyl]benzyl}carbamoylmethoxy)-2,3,4,5-tetrahydro-1,2,5-benzothiazepine;

1,1-dioxo-3,3-dibutyl-5-phenyl-7-methylthio-8-(N-{(R)-α[N-((S)-1-carboxy-2-(R)-hydroxypropyl)carbamoyl]benzyl}carbamoylmethoxy)-2,3,4,5-tetrahydro-1,2,5-benzothiazepine;

1,1-dioxo-3,3-dibutyl-5-phenyl-7methylthio-8(N-{(R)-α-[N-2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl) carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-1,2,5-benzothiadiazepine;

1,1-dioxo-3,3-dibutyl-5-phenyl-7-methylthio-8-(N-{(R)-α-[N-}(S)-1-[N-((S)-2-hydroxy-1-carboxyethyl)carbamoyl]propyl{carbamoy]benzyl}carbamoylmethoxy)-2,3,4,5-tetrahydro-1,2,5-benzothiadiazepine;

1,1-Dioxo-3,3-dibutyl-5-phenyl-7methylthio-8(N-{(R)-α-[N-((S)-1-carboxy-2-methylpropyl)carbamoyl]benzyl}carbamoylmethoxy)-2,3,4,5-tetrahhydro-1,2,5-benzothiadiazepine;

1,1-Dioxo-3,3-dibutyl-5-phenyl-7-methylthio-8(N-{(R)-α-[N-((S)-1-carboxypropyl) carbamoyl]-4-hydroxybenzyl}carbamoylmethoxy)-2,3,4,5-benzothiadiazepine;

1,1-Dioxo-3,3-dibutyl-5phenyl-7-methylthio-8-[N-((R/S)-α-{N-[1-(R)-2-(S)-1-hydroxy-1-(3,4-dihydroxyphenyl)prop-2-yl]carbamoyl}-4-hydroxbenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-5-(R)-2,3,4,5,6-pentahydroxyhexyl)carbamoyl]-4-hydroxybenzyl}carbamoylmethoxy)-2,3,4,5tetrahydro-1,2,5-benzothiadiazepine; and 1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoy]benzyl}carbamoylmethoxy)-2,3,4,5-tetrahydro-1,2,3-benzothiadiazepine; or a pharmaceutically a acceptable salt thereof.

* * * * *

UNITED STATES PATENT AND TRADEMARK OFFICE
CERTIFICATE OF CORRECTION

PATENT NO. : 7,462,644 B2           Page 1 of 7
APPLICATION NO. : 10/499893
DATED : December 9, 2008
INVENTOR(S) : Eva-Lotte Lindstedt Alstermark et al.

It is certified that error appears in the above-identified patent and that said Letters Patent is hereby corrected as shown below:

Column 23, line 50, Claim 2, delete "2ethoxy" and insert -- 2-ethoxy --.

Column 23, line 53, Claim 3, delete "(4Chlorobenzyl)" and insert -- (4-Chlorobenzyl) --.

Column 23, line 54, Claim 3, delete "{phenyl)" and insert -- }phenyl) --.

Column 23, line 56, Claim 4, after "ethyl" delete "[4(trifluoromethoxy" and insert -- [4-(trifluoromethoxy --.

Column 23, line 57, Claim 4, delete "amino }-" and insert -- amino}- --.

Column 23, line 59, Claim 5, delete "trifluommethyl" and insert -- trifluoromethyl --.

Column 23, line 62, Claim 6, delete "4-trifluoromethyl)" and insert -- 4-(trifluoromethyl) --.

Column 23, line 62, Claim 6, delete "amino{" and insert -- amino} -- .

Column 24, line 15, Claim 8, delete "trifluoromethy," and insert -- trifluoromethyl --.

Column 24, line 51, Claim 9, delete "$C_{2-6}$alkyl" and insert -- $C_{2-4}$ alkyl --.

Column 25, line 12, Claim 11, after "from" delete "(2S)-3-[4-(2-" and insert the same in the next line.

Column 25, line 13, Claim 11, delete "}[" and insert -- {[ --.

Column 25, line 13, Claim 11, delete "amino)-2" and insert -- amino}-2 --.

Column 25, line 14, Claim 11, delete "propanic" and insert -- propanoic --.

Column 25, line 16, Claim 11, delete "{phenyl" and insert -- }phenyl --.

Column 25, lines 17-18, Claim 11, delete "benzy-amino)" and insert -- benzyl-amino} --.

Column 25, lines 19-20, Claim 11, delete "benzy-amino)" and insert -- benzyl-ammo} --.

UNITED STATES PATENT AND TRADEMARK OFFICE
CERTIFICATE OF CORRECTION

PATENT NO.        : 7,462,644 B2
APPLICATION NO.  : 10/499893
DATED             : December 9, 2008
INVENTOR(S)       : Eva-Lotte Lindstedt Alstermark et al.

It is certified that error appears in the above-identified patent and that said Letters Patent is hereby corrected as shown below:

Column 25, line 33, Claim 16, delete "comprisinig" and insert -- comprising --.

Column 25, line 40, Claim 18, delete "1 dioxo3,3" and insert -- 1-dioxo-3,3 --.

Column 25, line 40, Claim 18, delete "dibutyl5phenyl7methylthio" and insert -- dibutyl-5-phenyl-7-methylthio --.

Column 25, line 40, Claim 18, delete "(N-}(R)" and insert -- (N-{(R) --.

Column 25, line 41, Claim 18, delete "1'[N'(carboxymethyl" and insert -- 1'-[N'-(carboxymethyl --.

Column 25, line 42, Claim 18, after "methyl" delete "{" and insert -- } --.

Column 25, line 42, Claim 18, delete "4.5tetrahydro" and insert -- 4,5-tetrahydro --.

Column 25, line 44, Claim 18, delete "1 dioxo3,3" and insert -- 1,1-dioxo-3,3 --.

Column 25, line 44, Claim 18, delete "5 phenyl7methylthio-8(N-}" and insert -- 5-phenyl-7-methylthio-8-(N-{ --.

Column 25, line 46, Claim 18, delete "{carbamoymethoxy)" and insert -- }carbamoylmethoxy) --.

Column 25, line 48, Claim 18, delete "1,1 dioxo-3," and insert -- 1,1-dioxo-3, --.

Column 25, line 48, Claim 18, delete "(N-}" and insert -- (N-{ --.

Column 25, line 49, Claim 18, delete "phenyl  1" and insert -- phenyl-1 --.

Column 25, line 50, Claim 18, delete "methyl{" and insert -- methyl} --.

Column 25, line 52, Claim 18, delete "1  dioxo3,3butyl" and insert -- 1-dioxo-3-butyl-3-ethyl --.

Column 25, line 52, Claim 18, delete "(N-}" and insert -- (N-{ --.

UNITED STATES PATENT AND TRADEMARK OFFICE
CERTIFICATE OF CORRECTION

PATENT NO. : 7,462,644 B2
APPLICATION NO. : 10/499893
DATED : December 9, 2008
INVENTOR(S) : Eva-Lotte Lindstedt Alstermark et al.

It is certified that error appears in the above-identified patent and that said Letters Patent is hereby corrected as shown below:

Column 25, line 52, Claim 18, delete "-α-" and insert -- -1'-phenyl-1' --.

Column 25, line 54, Claim 18, delete "-4hydroxybenzy{" and insert -- methyl} --.

Column 25, line 55, Claim 18, after "benzothiazepine" insert -- ; --.

Column 25, line 56, Claim 18, delete "3-butyl-3-ethyl" and insert -- 3,3-dibutyl --.

Column 25, line 56, Claim 18, delete "(N-}" and insert -- (N-{ --.

Column 25, line 57, Claim 18, delete "sulphoethyl)     carbamoy]" and insert -- sulphoethyl)carbamoyl] --.

Column 25, line 58, Claim 18, after "hydroxybenzyl" delete "{" and insert -- } --.

Column 25, lines 58-59, Claim 18, delete "tetrahtdro" and insert -- tetrahydro --.

Column 25, line 60, Claim 18, delete "dixo" and insert -- dioxo --.

Column 25, line 60, Claim 18, delete "-(N'-" and insert -- -(N-{(R)-α-[N' --.

Column 25, line 64, Claim 18, delete "methlthio" and insert -- methylthio --.

Column 26, lines 2-3, Claim 18, delete "carbamoy]-4-    hydroxybenzyl}" and insert -- carbamoyl]-4-hydroxybenzyl} --.

Column 26, line 6, Claim 18, delete "carboxyphenyl)carbonoyl]" and insert -- carboxypentyl)carbamoyl] --.

Column 26, line 7, Claim 18, delete "carbarnoylmethoxy" and insert -- carbamoylmethoxy --.

Column 26, line 8, Claim 18, delete "benzothiazepone;" and insert -- benzothiazepine; --.

Column 26, line 10, Claim 18, delete "dibuytl" and insert -- dibutyl --.

UNITED STATES PATENT AND TRADEMARK OFFICE
CERTIFICATE OF CORRECTION

PATENT NO. : 7,462,644 B2
APPLICATION NO. : 10/499893
DATED : December 9, 2008
INVENTOR(S) : Eva-Lotte Lindstedt Alstermark et al.

It is certified that error appears in the above-identified patent and that said Letters Patent is hereby corrected as shown below:

Column 26, lines 11-12, Claim 18, delete "carbarnoyl]    benzyl}" and insert
-- carbamoyl]benzyl} --.

Column 26, line 12, Claim 18, delete "carbarnoylmethoxy" and insert
-- carbamoylmethoxy --.

Column 26, line 14, Claim 18, delete "(N'-" and insert -- (N --.

Column 26, line 15, Claim 18, delete "sulphoethyl)    carbarnoyl" and insert
-- sulphoethyl)carbamoyl --.

Column 26, line 16, Claim 18, delete "carbarnoylmethoxy" and insert
-- carbamoylmethoxy --.

Column 26, line 19, Claim 18, delete "[(R)" and insert -- {(R) --.

Column 26, lines 19-20, Claim 18, delete "carbornoyl" and insert -- carbamoyl --.

Column 26, line 20, Claim 18, delete "{carbarnoylmethoxy" and insert
-- }carbamoylmethoxy --.

Column 26, line 22, Claim 18, delete "}(R)-" and insert -- {(R) --.

Column 26, line 24, Claim 18, after "benzyl" delete "{" and insert -- } --.

Column 26, line 26, Claim 18, delete "}N" and insert -- {N --.

Column 26, lines 28-29, Claim 18, after "carbamoylmethoxy" delete "{" and insert -- } --.

Column 26, line 31, Claim 18, delete "}α" and insert -- {α --.

Column 26, lines 31-32, Claim 18, delete "carbamoy]    benzyl{" and insert
-- carbamoyl]benzyl} --.

Column 26, line 35, Claim 18, delete "methylyhio" and insert -- methylthio --.

UNITED STATES PATENT AND TRADEMARK OFFICE
CERTIFICATE OF CORRECTION

PATENT NO. : 7,462,644 B2
APPLICATION NO. : 10/499893
DATED : December 9, 2008
INVENTOR(S) : Eva-Lotte Lindstedt Alstermark et al.

It is certified that error appears in the above-identified patent and that said Letters Patent is hereby corrected as shown below:

Column 26, line 36, Claim 18, delete "}α-N'" and insert -- {α-[N' --.

Column 26, line 37, Claim 18, delete "benzyl{" and insert -- benzyl} --.

Column 26, line 39, Claim 18, delete "}N-" and insert -- {N --.

Column 26, line 40, Claim 18, delete "methyl)" and insert -- (methyl) --.

Column 26, lines 40-41, Claim 18, delete "phosphoryl]   ethyl{" and insert
    -- phosphoryl]ethyl}carbamoyl)benzyl] --.

Column 26, line 44, Claim 18, delete "carbamoy]" and insert -- carbamoyl] --.

Column 26, line 47, Claim 18, delete "methylyhio" and insert -- methylthio --.

Column 26, line 48, Claim 18, delete "-N'-" and insert -- -(N'- --.

Column 26, lines 49-50, Claim 18, after "carbamoylmethoxy" delete "{" and insert -- } --.

Column 26, line 50, Claim 18, delete "5benzothiazepine;" and insert
    -- 5-benzothiazepine; --.

Column 26, line 51, Claim 18, delete "methythio-8-}" and insert -- methylthio-8-{ --.

Column 26, line 52, Claim 18, delete "phosphory]" and insert -- phosphoryl] --.

Column 26, line 53, Claim 18, delete "{carbomoyl" and insert -- }carbamoyl --.

Column 26, line 55, Claim 18, after "(R)-" insert -- α-[(R) --.

Column 26, line 64, Claim 18, delete "methylythio" and insert -- methylthio --.

Column 27, line 3, Claim 18, delete "hydroxbenzyl}" and insert -- hydroxybenzyl} --.

Column 27, line 3, Claim 18, after "2,3,4,5-" insert -- tetrahydro-1,2,5 --.

UNITED STATES PATENT AND TRADEMARK OFFICE
CERTIFICATE OF CORRECTION

PATENT NO. : 7,462,644 B2
APPLICATION NO. : 10/499893
DATED : December 9, 2008
INVENTOR(S) : Eva-Lotte Lindstedt Alstermark et al.

It is certified that error appears in the above-identified patent and that said Letters Patent is hereby corrected as shown below:

Column 27, lines 7-8, Claim 18, delete "tetrahhydro-" and insert -- tetrahydro --.

Column 27, line 10, Claim 18, delete "1carboxybutyl" and insert -- 1-carboxybutyl --.

Column 27, line 14, Claim 18, delete "5phenyl" and insert -- 5-phenyl --.

Column 27, line 14, Claim 18, delete "-N-" and insert -- (N --.

Column 27, line 23, Claim 18, delete "α[N-" and insert -- α-[N- --.

Column 27, line 26, Claim 18, delete "7methylthio-8(N" and insert
    -- 7-methylthio-8-(N --.

Column 27, line 27, Claim 18, delete "[N-2-" and insert -- [N-(2 --.

Column 28, line 3, Claim 18, delete "2,3,4,5-1,2,5" and insert
    -- 2,3,4,5-tetrahydro-1,2,5 --.

Column 28, line 6, Claim 18, delete "-}(S)" and insert -- -{(S) --.

Column 28, lines 7-8, Claim 18, delete "{carbamoy]      benzyl}" and insert
    -- }carbamoyl]benzyl} --.

Column 28, line 10, Claim 18, delete "Dioxo" and insert -- dioxo --.

Column 28, line 10, Claim 18, delete "7methylthio-8(N" and insert
    -- 7-methylthio-8-(N --.

Column 28, line 12, Claim 18, delete "tetrahhydro" and insert -- tetrahydro --.

Column 28, line 14, Claim 18, delete "8(N" and insert -- 8-(N --.

Column 28, line 16, Claim 18, after "2,3,4,5-" insert -- tetrahydro-1,2,5 --.

Column 28, line 18, Claim 18, delete "5phenyl" and insert -- 5-phenyl --.

Column 28, line 20, Claim 18, delete "hydroxbenzyl" and insert -- hydroxybenzyl --.

UNITED STATES PATENT AND TRADEMARK OFFICE
CERTIFICATE OF CORRECTION

PATENT NO.        : 7,462,644 B2
APPLICATION NO.   : 10/499893
DATED             : December 9, 2008
INVENTOR(S)       : Eva-Lotte Lindstedt Alstermark et al.

It is certified that error appears in the above-identified patent and that said Letters Patent is hereby corrected as shown below:

Column 28, line 24, Claim 18, delete "3-(R)-5-(R)     -2,3,4,5,6-" and insert -- 3-(R)-4-(R)-5-(R)-2,3,4,5,6 -- .

Column 28, line 27, Claim 18, delete "5tetrahydro" and insert -- 5-tetrahydro --.

Column 28, line 29, Claim 18, delete "4-(R)   -5-(R) -    2,3,4,5,6-" and insert -- 4-(R)-5-(R)-2,3,4,5,6 --.

Column 28, line 30, Claim 18, delete "carbamoy]" and insert -- carbamoyl] --.

Column 28, line 31, Claim 18, delete "-1,2,3-" and insert -- -1,2,5 --.

Column 28, line 32, Claim 18, after "pharmaceutically" delete "a".

Signed and Sealed this

Seventh Day of April, 2009

JOHN DOLL
*Acting Director of the United States Patent and Trademark Office*